(12) United States Patent
Zhang et al.

(10) Patent No.: US 12,629,411 B2
(45) Date of Patent: May 19, 2026

(54) N PROTEIN EPITOPE MUTATION MARKER FOR PREPARING EPITOPE DELETION-MARKED VACCINE STRAIN OF TYPE II PORCINE REPRODUCTIVE AND RESPIRATORY SYNDROME VIRUS (PRRSV) AND USE THEREOF

(71) Applicant: Lanzhou Veterinary Research Institute, Chinese Academy of Agricultural Sciences, Lanzhou (CN)

(72) Inventors: Jing Zhang, Lanzhou (CN); Zengjun Lu, Lanzhou (CN); Kun Li, Lanzhou (CN); Pu Sun, Lanzhou (CN); Jian Wang, Lanzhou (CN); Yimei Cao, Lanzhou (CN); Huifang Bao, Lanzhou (CN); Zhixun Zhao, Lanzhou (CN); Pinghua Li, Lanzhou (CN); Yuanfang Fu, Lanzhou (CN); Xueqing Ma, Lanzhou (CN); Hong Yuan, Lanzhou (CN); Xingwen Bai, Lanzhou (CN); Qiang Zhang, Lanzhou (CN); Dong Li, Lanzhou (CN); Zaixin Liu, Lanzhou (CN)

(73) Assignee: LANZHOU VETERINARY RESEARCH INSTITUTE, CHINESE ACADEMY OF AGRICULTURAL SCIENCES, Lanzhou (CN)

( * ) Notice: Subject to any disclaimer, the term of this patent is extended or adjusted under 35 U.S.C. 154(b) by 784 days.

(21) Appl. No.: 17/997,749

(22) PCT Filed: Mar. 17, 2022

(86) PCT No.: PCT/CN2022/081330
§ 371 (c)(1),
(2) Date: Nov. 2, 2022

(87) PCT Pub. No.: WO2023/123696
PCT Pub. Date: Jul. 6, 2023

(65) Prior Publication Data
US 2024/0148850 A1 May 9, 2024

(30) Foreign Application Priority Data

Dec. 29, 2021 (CN) .......................... 202111638189.3

(51) Int. Cl.
| | |
|---|---|
| *A61K 39/00* | (2006.01) |
| *A61K 39/12* | (2006.01) |
| *C07K 14/005* | (2006.01) |
| *G01N 33/569* | (2006.01) |

(52) U.S. Cl.
CPC ............ *A61K 39/12* (2013.01); *C07K 14/005* (2013.01); *G01N 33/56983* (2013.01); *A61K 2039/5252* (2013.01); *A61K 2039/5254* (2013.01); *C12N 2770/10022* (2013.01); *C12N 2770/10034* (2013.01); *G01N 2333/08* (2013.01)

(58) Field of Classification Search
None
See application file for complete search history.

(56) References Cited

U.S. PATENT DOCUMENTS

| | | | |
|---|---|---|---|
| 2014/0335118 A1* | 11/2014 | Wang ...................... | A61P 37/04 |
| | | | 435/5 |
| 2024/0148850 A1* | 5/2024 | Zhang ................... | A61K 39/12 |

OTHER PUBLICATIONS

An et al. (Virus Genes. 2005; 31 (1): 81-87).*
A machine translation of CN 113336845, corresponding to patent (application) 202110598030.7 published Sept 3, 2021.*
George et al. (Circulation. 1998; 97: 900-906).*
He et al. (Vaccines. 2025; 13; 260).*
Wootton et al. (Clinical and Diagnostic Laboratory Immunology. 1998; 5 (6): 773-779).*
Rappe et al. (Veterinary Research. 2016; 47: 117).*

* cited by examiner

*Primary Examiner* — Shanon A. Foley
(74) *Attorney, Agent, or Firm* — Tutunjian & Bitetto, P.C.

(57) ABSTRACT

The present disclosure provides an N protein epitope mutation marker for preparing an epitope deletion-marked vaccine strain of type II porcine reproductive and respiratory syndrome virus (PRRSV) and use thereof, belonging to the technical field of biological products. In the mutation marker, one or more amino acids are mutated based on an epitope sequence at positions 92 to 103 of a C-terminal of an N protein of the type II PRRSV; and the epitope mutation marker has an amino acid sequence shown in SEQ ID NO: 1, where $X_1$ is selected from the group consisting of T, P, and A; and $X_2$ is selected from the group consisting of V and A.

2 Claims, 7 Drawing Sheets

Specification includes a Sequence Listing.

83-85A  86-88A  89-91A  92-94A  95-97A  98-100A  101-103A  104-106A  107-109A  110-112A

L92A  S93A  D94A  S95A  G96A  R97A  I98A  S99A  Y100A  T101A  V102A  E103A

C8

GST

N PROTEIN EPITOPE MUTATION MARKER FOR PREPARING EPITOPE DELETION-MARKED VACCINE STRAIN OF TYPE II PORCINE REPRODUCTIVE AND RESPIRATORY SYNDROME VIRUS (PRRSV) AND USE THEREOF

CROSS REFERENCE TO RELATED APPLICATION

The present application claims priority to the Chinese Patent Application No. 202111638189.3, filed with the China National Intellectual Property Administration (CNIPA) on Wednesday, Dec. 29, 2021, intended to and entitled "N PROTEIN EPITOPE MUTATION MARKER FOR PREPARING EPITOPE DELETION-MARKED VACCINE STRAIN OF TYPE II PORCINE REPRODUCTIVE AND RESPIRATORY SYNDROME VIRUS (PRRSV) AND USE THEREOF", which is incorporated herein by reference in its entirety.

REFERENCE TO SEQUENCE LISTING

A computer readable txt file entitled "SEQUENCE LISTING. txt", that was created on Jan. 5, 2026, with a file size of 32,852 bytes, contains the sequence listing for this application, has been filed with this application, and is hereby incorporated by reference in its entirety.

TECHNICAL FIELD

The present disclosure belongs to the technical field of biological products, and in particular relates to an N protein epitope mutation marker for preparing an epitope deletion-marked vaccine strain of type II porcine reproductive and respiratory syndrome virus (PRRSV) and use thereof.

BACKGROUND ART

Porcine reproductive and respiratory syndrome (PRRS) is a highly-contagious infectious disease caused by porcine reproductive and respiratory syndrome virus (PRRSV) that seriously endangers swine industry in the world. The PRRS mainly causes respiratory diseases in piglets and fattening pigs and reproductive disorders in sows, causing a huge economic loss to the global swine industry. The PRRSV, as a single-stranded, positive-sense RNA virus with a genome of about 15 kb, mainly infects antigen-presenting cells such as pulmonary alveolar macrophages (PAM), mature monocytes, and microglia.

Although vaccine immunization has a certain effect on the control of PRRS, vaccines, including attenuated vaccines and inactivated vaccines, have some shortcomings. The attenuated vaccines may have safety issues including reverting to virulence and recombination of field epidemic strain and vaccine strain. Excessive clinical use of attenuated vaccine strains may further promote virus recombination and mutation, complicating the epidemic situation. The inactivated vaccines have better protection against homologous strains, but insufficient cross-immune protection against heterologous pandemic strains. With the continuous emergence of recombinant mutant strains, more and more experts realize that attention should be paid to the use of the inactivated vaccines to change the complex situation of PRRS control.

At present, neither attenuated nor inactivated vaccines can effectively distinguish naturally-infected animals from vaccine-immunized animals, so it is impossible to evaluate the infection status and purify the disease in immunized swine herd. Therefore, it is a focus of current researches on PRRS control products by preparing a negatively-marked vaccine of epitope deletion for PRRS. There are methods in the prior art for distinguishing between PRRSV natural infection and vaccine immunization. For example, after immunization with the vaccine, animals do not produce antibodies against a linear epitope of an M protein for PRRSV American strain; detection of the antibodies make it possible to distinguish between naturally-infected animals and vaccine-immunized animals (CN105749267A, Jul. 13, 2016). For another example, a method to distinguish vaccine immunity from natural infection for *Brucella abortus* is to simultaneously detect IgG and IgM in one sample (CN108037277A, May 15, 2018). In addition, target genes or polypeptide sites are knocked out by homologous recombination, and vaccine-immunized animals are distinguished from wild bacteria-infected animals by detecting the target genes or polypeptides (CN111057671A, Apr. 24, 2020; CN104165998A, August 2016). Although the construction of vaccines with epitope deletion is convenient for subsequent differentiation and identification, there are strict restrictions on deletion sites. Inappropriate deletion of epitopes may reduce the immunogenicity of vaccine antigens, resulting in reduced immune efficacy of vaccines.

SUMMARY

In view of this, a purpose of the present disclosure is to provide a linear and non-neutralizing epitope mutation marker locus of the N protein of PRRSV. An epitope deletion-marked inactivated or attenuated vaccine can be prepared based on the site, to distinguish animals naturally infected with the PRRSV from animals immunized with a whole-virus vaccine.

The present disclosure provides an N protein linear and non-neutralizing epitope mutation marker for preparing an epitope deletion-marked vaccine strain of type II PRRSV, where one or more amino acids are mutated based on an amino acid sequence at positions 92 to 103 of a C-terminal of an N protein of the type II PRRSV; and the N protein epitope mutation marker has an amino acid sequence shown in SEQ ID NO: 1, where $X_1$ is selected from the group consisting of T, P, and A; and $X_2$ is selected from the group consisting of V and A.

Preferably, when one amino acid locus is mutated, serine at position 93 may be mutated.

Preferably, when multiple amino acids are mutated, 2 to 12 continuous or discontinuous amino acids may be mutated.

Preferably, 3 to 9 continuous or discontinuous ones of the amino acids may be mutated.

Preferably, 3 continuous or discontinuous amino acids may be mutated.

Preferably, 3 amino acid residues of LSD may be mutated at positions 92 to 94, 3 amino acid residues of GRI may be mutated at positions 95 to 97, 3 amino acid residues of $SYX_1$ may be mutated at positions 98 to 100, or 3 amino acid residues of $X_2EF$ may be mutated at positions 101 to 103.

Preferably, the mutation may include mutational modification, deletion or insertion of a heterologous sequence.

Preferably, the mutational modification may include amino acid substitution.

Preferably, the amino acid substitution may be conducted with alanine.

The present disclosure further provides a whole-virus vaccine with epitope deletion of PRRSV, where the vaccine is PRRSV including the N protein epitope mutation marker.

Preferably, the PRRSV may be type II PRRSV.

The present disclosure further provides the use of a porcine single B cell antibody C8 of PRRSV N protein in the preparation of a reagent or a kit for detecting the vaccine with epitope deletion of PRRSV. The amino acid sequence of the porcine single B cell antibody C8 comprises the heavy chain variable region amino acid sequence HV1 (SEQ ID No: 63: GLVQPGGSLRLSCVASGFTFSSYIVTWVRQSPGK-GLEWLAGTGVGEYALYYRNSVRGRF TLSRDNSQN-TAYLQMNSLRVEETGRYFCRR-GAAESVDLWGPGVEVVVSS) and the light chain variable region amino acid sequence LV1 (SEQ ID No: 64: QEPAMSVSLGGTVTLTCAFSSGSVTRSH-WPSWFQLTPGQPPRTLIVSTDSRPTGVPSRFSG AIS-GYKAALTITGAQPEDEAD-YVCGVYFTFTKRPFGGGTHLTVLG).

The present disclosure further provides the use of a porcine single B cell antibody C8 of PRRSV N protein in distinguishing PRRSV natural infection and immunization by PRRSV vaccines.

The present disclosure provides the N protein epitope mutation marker for preparing the epitope deletion-marked vaccine strain of the type II PRRSV, where one or more of the amino acids are mutated based on the amino acid sequence at positions 92 to 103 of the C-terminal of the N protein of the type II PRRSV. The epitope mutation marker has the amino acid sequence shown in SEQ ID NO: 1, where $X_1$ is selected from the group consisting of T, P, and A; and $X_2$ is selected from the group consisting of V and A. In the present disclosure, a non-protective dominant epitope in the C-terminal of the N protein of the type II PRRSV is identified. Mutation of the epitope can effectively distinguish between naturally-infected animals and animals immunized with a whole-virus vaccine of epitope deletion. The marker provides a technical basis for formulating and implementing a prevention and control strategy for PRRSV immunologic purging.

BRIEF DESCRIPTION OF THE DRAWINGS

as shown in FIG. 7, "majority" represents a conserved sequence, and its amino acid sequence is set forth in SEQ ID NO: 48; the amino acid sequence of the N protein from JXwn06 is set forth in SEQ ID NO: 49, the amino acid sequence of the N protein from GSWW is set forth in SEQ ID NO: 50, the amino acid sequence of the N protein from HuN4 is set forth in SEQ ID NO: 51, the amino acid sequence of the N protein from SHH is set forth in SEQ ID NO: 52, the amino acid sequence of the N protein from JXA1-P170 is set forth in SEQ ID NO: 53, the amino acid sequence of the N protein from CH1a is set forth in SEQ ID NO: 54, the amino acid sequence of the N protein from VR2332 is set forth in SEQ ID NO: 55, the amino acid sequence of the N protein from FL-12 is set forth in SEQ ID NO: 56, the amino acid sequence of the N protein from MN184A is set forth in SEQ ID NO: 57, the amino acid sequence of the N protein from MN184B is set forth in SEQ ID NO: 58, the amino acid sequence of the N protein from MN184C is set forth in SEQ ID NO: 59, the amino acid sequence of the N protein from HKEU16 is set forth in SEQ ID NO: 60, the amino acid sequence of the N protein from LV is set forth in SEQ ID NO: 61, and the amino acid sequence of the N protein from LDV is set forth in SEQ ID NO: 62.

DETAILED DESCRIPTION OF THE EMBODIMENTS

Figure 1:
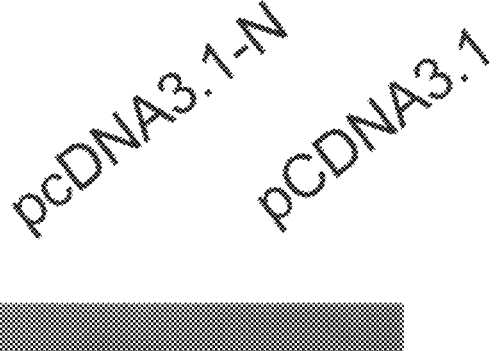
FIG. 1 shows the results of Western blotting with C8 and GAPDH antibodies after transfecting a pcDNA3.1-N and a pcDNA3.1 empty vector in 293T cells.
Figure 1:
Figure 1:
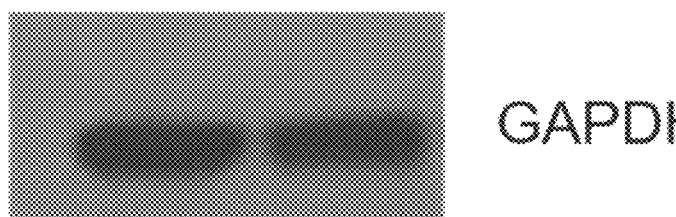

The present disclosure provides an N protein epitope mutation marker locus for preparing an epitope deletion-marked vaccine strain of type II PRRSV, where one or more amino acids are mutated based on an amino acid sequence at positions 92 to 103 of a C-terminal of an N protein of the type II PRRSV. The N protein epitope mutation marker has an amino acid sequence shown in SEQ ID NO: 1, where $X_1$ is selected from the group consisting of T, P, and A; and $X_2$ is selected from the group consisting of V and A.

In the present disclosure, the N protein epitope mutation marker locus has the amino acid sequence shown in SEQ ID NO: 1 (LSDGRISYX$_1$X$_2$EF). In different PRRSV strains, sequences of polypeptides at positions 92 to 103 at the C-terminal of the N protein are not completely conserved, and there are amino acid variations at positions 100 and 101; $X_1$ can be T, P, or A, and $X_2$ can be V or A. A source strain of the epitope includes preferably type II strains such as GSWW/2015, MN184A, MN184B, and JX$_{WN}$06.

In the present disclosure, the mutation includes preferably deletion or substitution. The substitution involves preferably substituting an amino acid at any position in an epitope sequence with another type of amino acid, such as alanine. Preferably, when one amino acid locus is mutated, serine at position 93 is mutated. The research results of an example show that reactivity of the serine at position 93 after mutation with C8 is significantly reduced, indicating that the serine at position 93 is the most critical locus for C8 antibody recognition. Preferably, when multiple amino acids are mutated, 2 to 12 continuous or discontinuous amino acids, more preferably 3 to 9 amino acids are mutated. Preferably, three amino acid residues of LSD are mutated at positions 92 to 94, three amino acid residues of GRI are mutated at positions 95 to 97, three amino acid residues of SYX$_1$ are mutated at positions 98 to 100, or three amino acid residues of X$_2$EF are mutated at positions 101 to 103. The results of an example show that proteins with three point mutations of amino acid sequences at positions 92 to 103 do not react with the C8 antibody, indicating that positions 92 to 103 are the epitope recognized by C8 antibody; altering one or several amino acid loci can eliminate the epitope recognized by C8 antibody. After immunizing animals with epitope-deleted N protein and natural N protein, the two protein-immunized animals can be distinguished by detecting C8 epitope antibody. Therefore, if the deletion marker locus is introduced into a whole-virus vaccine, marked vaccine-immunized animals and naturally-infected animals can be accurately distinguished, achieving the goal of accurately identifying PRRSV infection and immunized animals. This can provide technical and product supports for status monitoring and immune purification of type II PRRSV infection.

Based on the epitope deletion at positions 92 to 103 of the N protein of the type II PRRSV, accurate identification of the animals immunized with natural N protein and epitope-deleted N protein can be realized. Therefore, the present disclosure provides a preparation method of an N protein epitope deletion-marked whole-virus vaccine for the type II PRRSV.

In the present disclosure, the PRRSV strain is preferably PRRSV American type strain, namely the type II PRRSV. A vaccine strain includes preferably strains such as GSWW/2015 and GSWW/2018.

In the present disclosure, the linear epitope mutation marker locus is derived from the N protein. The N protein has relatively high conservation and immunogenicity, and N protein antibodies can be detected in serum about 7 d after infection; however, the N protein antibodies have no neutralizing activity. Therefore, the original immunogenicity and immune protection effect of the whole-virus vaccine are not affected by carrying the linear epitope mutation marker locus in the whole-virus vaccine.

In the present invention, there is no particular limitation on construction methods of the whole-virus vaccine of epitope mutation for PRRSV, and construction methods of an epitope-deleted vaccine well known in the art can be used. In an example, a gene encoding the N protein is mutated preferably by genetic engineering, and a mutated N protein gene sequence is cloned into PRRSV full-length plasmid, and the whole-virus vaccine of epitope mutation for PRRSV is obtained through virus rescue.

The present disclosure further provides the use of a porcine single B cell antibody C8 of PRRSV N protein in preparation of a detection kit for distinguishing PRRSV natural infection and the animals immunized with the whole-virus vaccine of epitope deletion for PRRSV.

In the present disclosure, the porcine single B cell antibody C8 of PRRSV N protein is disclosed in patent 202110598030.7. The kit is preferably prepared based on ELISA. The ELISA is preferably competitive ELISA. The kit further includes preferably an antigen reaction plate, a 100× concentrated biotin-labeled antibody, 100× concentrated enzyme-labeled avidin, a 25× concentrated washing solution, a serum diluent, a substrate solution, a stop solution, a positive control serum and a negative control serum. For specific ingredients, see patent 202110598030.7.

In the present disclosure, a detection method of the kit includes preferably the following steps:

immunizing an animal by PRRSV wild-type strain and the whole-virus vaccine of epitope mutation for PRRSV separately, and collecting two groups of antisera;

adding the antisera to an antigen reaction plate of the kit, after incubation, washing to obtain a reaction plate;

adding a biotin-labeled C8 antibody to the reaction plate, after incubation, washing to obtain a reaction plate after competing reaction; and adding HRP-labeled avidin to the reaction plate after competing reaction, washing after incubation, adding a substrate for a reaction, terminating the reaction, and measuring an absorbance value.

In the present disclosure, the competitive ELISA method of PRRSV N protein antibody can well distinguish wild-type and epitope-deleted N protein immune sera, thereby distinguishing between naturally-infected animals and animals immunized with whole-virus vaccine of N protein epitope deletion.

To further illustrate the present disclosure, the N protein epitope mutation marker for preparing an epitope deletion-marked vaccine strain of type II PRRSV and the use thereof provided by the present disclosure are described in detail below in connection with examples, but these examples should not be understood as limiting the claimed scope of the present disclosure.

Example 1

Experiment on Specific Binding of C8 Antibody to N Protein of PRRSV American Type Strain A gene sequence (SEQ ID NO: 2, AAGCTTAC-CATGTACCCATACGACGTCCCAGACTACGCTC-CAAATAACAACGGCAAG CAGCAAAAGAAAAAGAAGGG-GAATGGCCAGCCAGTCAATCAGCTGTGC-CAAATGCT GGGTAAGATCATCGCC-CAACAAAATCAGTCCAGAGGCAAGGGACCGGGGA AGAAAA ATAGGAAGAAAAACCCGGAGAAGCCC-CATTTCCCTCTAGCGACTGAAGATGACGTCA GGCATCACTTTACCCCTAGTGAGCGGCAAT-TGTGTCTGTCGTCGATCCAGACTGCCTT CAACCAGGGCGCTGGAACTTGTGCCCTGTCAGAT-TCAGGGAGGATAAGTTACACTGT GGAGTT-TAGTTTGCCGACGCAACATACTGTGCGTCT-GATCCGCGCCACAGCATCACCC TCAGCAGACTA-CAAGGACGACGACGACAAGGGCGACTACAAA-GATGACGATGATAA GATCGATTACAAAGAC-GATGACGATAAGTGAGAATTC) of a CDS region of an N protein of a GSWW/2015 strain was synthesized, and inserted into Hind III and ECOR I of a pCDNA3.1 vector; a pCDNA3.1 empty vector and a pcDNA3.1-N plasmid were extracted with an endotoxin-free plasmid extraction kit separately, and 293T cells were transfected with Lipo3000 for 24 h; the cells were lysed on ice with an RIPA (Beyotime P0013) lysis buffer for 30 min, and centrifuged at 12,000 rpm for 10 min at 4° C., and a total protein was extracted. A loading buffer was added for treatment at 95° C. for 5 min; after protein denaturation, SDS-PAGE was conducted using a 4% to 12% acrylamide gel; the protein was transferred to a PVDF membrane, blocked with a 5% skim milk powder for 1 h, and incubated with a C8 antibody (1:1000) at 4° C. overnight. After washing three times with a TBST solution, an HRP-labeled goat anti-pig secondary antibody (sigma, 1:10000) was added, and incubated for 1 h at room temperature; after washing with the TBST solution three times, a chemiluminescent solution (Thermo fisher, Pierce ECL Plus) was added, and exposed to film in a dark room after 5 min.

The results are shown in FIG. 1. The results show that the C8 antibody binds to the N protein of PRRSV.

Example 2

Preliminary Identification of C8 Recognizing Epitope of N Protein by Synthetic Peptide ELISA The N protein of GSWW15 was segmented to synthesize polypeptides, where a corresponding relationship between names and sequences of each polypeptide was shown in Table 1. The polypeptides were dissolved in a carbonate solution (Sigma) at a concentration of 50 μg/ml, where 100 μl of the polypeptides were added to each well of a 96-well plate, and then incubated overnight at 4° C. A biotin-labeled 0.25 μg/ml C8 antibody was added, reaction was conducted at 37° C. for 1 h, a reaction product was washed 5 times with PBST, and dried by patting for the last time. 100 μl of HRP-labeled avidin was added, reaction was conducted at 37° C. for 1 h, a reaction product was washed 5 times with PBST, and dried by patting for the last time. A substrate solution [3,3',5,5'-tetramethylbenzidine (TMB) substrate] was added, reaction was conducted at 37° C. in the dark for 15 min, a stop solution (0.3 mol/L $H_2SO_4$ solution) was added, and absorbance was measured at 450 nm within 10 min.

TABLE 1

Information on each peptide fragment of N protein of GSWW15

| Polypeptide name | Amino acid sequence | Sequence No. |
| --- | --- | --- |
| GSWW15 N1 | MPNNNGKQQKKKKGN | (SEQ ID NO: 3) |
| GSWW15 N2 | GKQQKKKKGNGQPVN | (SEQ ID NO: 4) |
| GSWW15 N3 | KKKGNGQPVNQLCQM | (SEQ ID NO: 5) |
| GSWW15 N4 | GQPVNQLCQMLGKII | (SEQ ID NO: 6) |
| GSWW15 N5 | QLCQMLGKIIAQQNQ | (SEQ ID NO: 7) |
| GSWW15 N6 | LGKIIAQQNQSRGKG | (SEQ ID NO: 8) |
| GSWW15 N7 | AQQNQSRGKGPGKKN | (SEQ ID NO: 9) |
| GSWW15 N8 | SRGKGPGKKNRKKNP | (SEQ ID NO: 10) |
| GSWW15 N9 | PGKKNRKKNPEKPHF | (SEQ ID NO: 11) |
| GSWW15 N10 | RKKNPEKPHFPLATE | (SEQ ID NO: 12) |
| GSWW15 N11 | EKPHFPLATEDDVRH | (SEQ ID NO: 13) |
| GSWW15 N12 | PLATEDDVRHHFTPS | (SEQ ID NO: 14) |
| GSWW15 N13 | DDVRHHFTPSERQLC | (SEQ ID NO: 15) |
| GSWW15 N14 | HFTPSERQLCLSSIQ | (SEQ ID NO: 16) |
| GSWW15 N15 | ERQLCLSSIQTAFNQ | (SEQ ID NO: 17) |
| GSWW15 N16 | LSSIQTAFNQGAGTC | (SEQ ID NO: 18) |
| GSWW15 N17 | TAFNQGAGTCALSDS | (SEQ ID NO: 19) |
| GSWW15 N18 | GAGTCALSDSGRISY | (SEQ ID NO: 20) |
| GSWW15 N19 | ALSDSGRISYTVEFS | (SEQ ID NO: 21) |
| GSWW15 N20 | GRISYTVEFSLPTQH | (SEQ ID NO: 22) |

TABLE 1-continued

Information on each peptide fragment of N protein of GSWW15

| Polypeptide name | Amino acid sequence | Sequence No. |
| --- | --- | --- |
| GSWW15 N21 | TVEFSLPTQHTVRLI | (SEQ ID NO: 23) |
| GSWW15 N22 | LPTQHTVRLIRATAS PSA | (SEQ ID NO: 24) |
| GSWW18 N1 | MPNNNGRQQNKKKGD | (SEQ ID NO: 25) |
| GSWW18 N2 | GRQQNKKKGDGQPVN | (SEQ ID NO: 26) |
| GSWW18 N3 | KKKGDGQPVNQLCQM | (SEQ ID NO: 27) |
| GSWW18 N4 | GQPVNQLCQMLGKIIA | (SEQ ID NO: 28) |
| GSWW18 N5 | QLCQMLGKIIAQQRQS | (SEQ ID NO: 29) |
| GSWW18 N6 | LGKIIAQQRQSKGRG | (SEQ ID NO: 30) |
| GSWW18 N7 | AQQRQSKGRGPGKKN | (SEQ ID NO: 31) |
| GSWW18 N8 | SKGRGPGKKNKNKNL | (SEQ ID NO: 32) |
| GSWW18 N9 | PGKKNKNKNLEKPHF | (SEQ ID NO: 33) |
| GSWW18 N10 | KNKNLEKPHFPLATE | (SEQ ID NO: 34) |
| GSWW18 N11 | EKPHFPLATEDDVRH | (SEQ ID NO: 35) |
| GSWW18 N12 | PLATEDDVRHHFTPS | (SEQ ID NO: 36) |
| GSWW18 N13 | DDVRHHFTPSERQLC | (SEQ ID NO: 37) |
| GSWW18 N14 | HFTPSERQLCLSSIR | (SEQ ID NO: 38) |
| GSWW18 N15 | ERQLCLSSIRTAFNQ | (SEQ ID NO: 39) |
| GSWW18 N16 | LSSIRTAFNQGAGTC | (SEQ ID NO: 40) |
| GSWW18 N17 | TAFNQGAGTCTLSDS | (SEQ ID NO: 41) |
| GSWW18 N18 | GAGTCTLSDSGRISY | (SEQ ID NO: 42) |
| GSWW18 N19 | TLSDSGRISYTVEFS | (SEQ ID NO: 43) |
| GSWW18 N20 | GRISYTVEFSLPTHH | (SEQ ID NO: 44) |
| GSWW18 N21 | TVEFSLPTHHTVRLI | (SEQ ID NO: 45) |
| GSWW18 N22 | LPTHHTVRLIRVTTS PSA | (SEQ ID NO: 46) |

Figure 2:
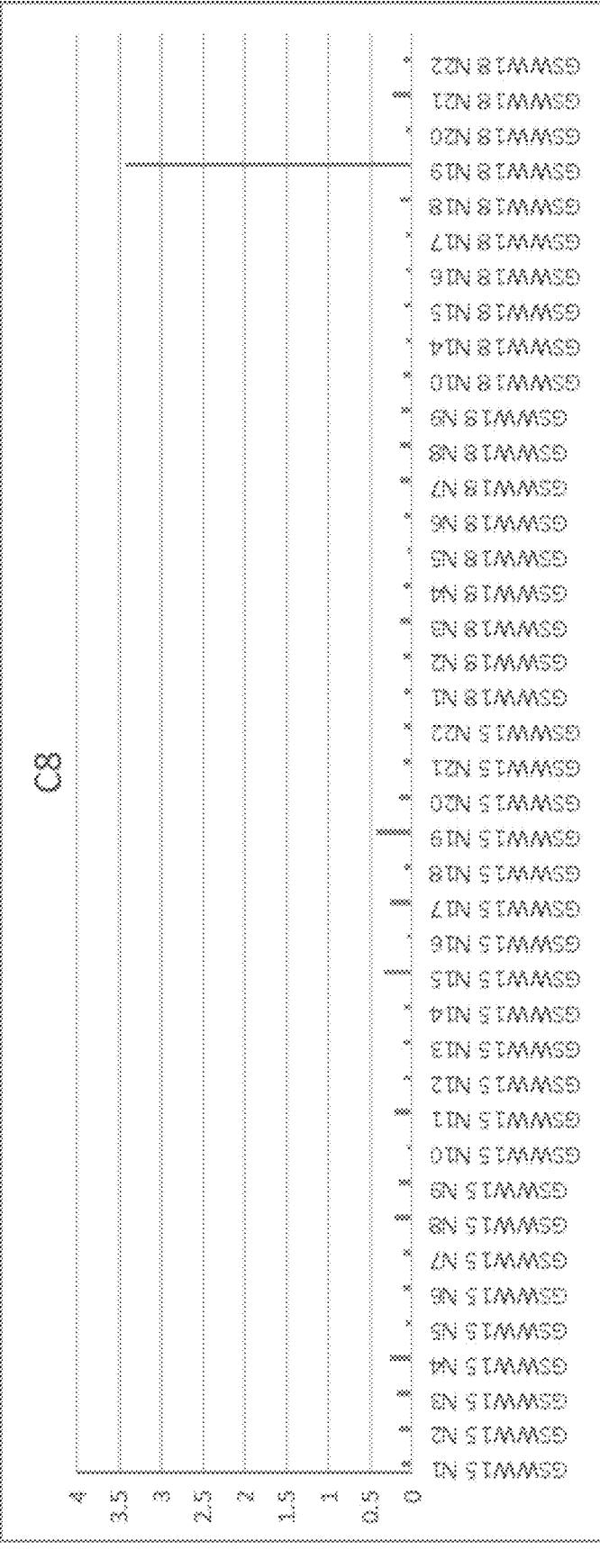
FIG. 2 shows the results of a reaction between a C8 monoclonal antibody and an N19 peptide fragment of the N protein detected by synthetic peptide ELISA.

The results were shown in FIG. 2. The results show that the C8 monoclonal antibody reacts with the N19 peptide fragment, indicating that the N19 peptide fragment contains the epitope of the C8 monoclonal antibody.

Example 3

GST Fusion Protein Identification of Key Loci of N Protein Epitope

Positions 83 to 112 of an N protein of a GSWW/2018 strain was mutated into alanine by three point mutations (a gene for point mutation was synthesized by a company and ligated to a vector through BamHI and XhoI; the alanine had a relatively simple scanning structure and was easy to identify, a purpose was only to destroy the epitope), and a mutant gene was synthesized and cloned into a pGEX-6T-1 vector. The plasmids containing different mutants were transformed into BL-21 competent cells, and single clones were selected and incubated overnight. IPTG with a final concentration of 1 mmol/L was added to induce for 6 h, and supernatants were added for Western blotting.

Figures 3, 4:
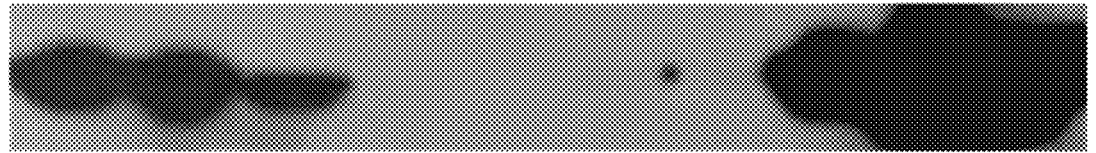
FIG. 3 shows reactivity detection results of peptides at positions 83 to 112 of the N protein with C8 monoclonal antibody after three consecutive point mutations.
FIG. 4 shows reactivity detection results of peptides at positions 92 to 103 of the N protein with C8 monoclonal antibody after single point mutation.

The results are shown in FIG. 3. The results show that none of the proteins after three point mutations at positions 92 to 103 reacts with the C8 antibody, proving that positions 92 to 103 were the epitopes recognized by the C8 antibody.

Example 4

The Experiment of Epitope Deletion Caused by Mutation at Positions 92 to 94 of N Protein An N protein of a GSWW/2018 strain and a gene (SEQ ID NO: 47, GGATCCATGC-CAAATAACAACGGCAAGCAGCAAAAGAAAAAGA AGGGGAATGGCCA GCCAGTCAATCAGCTGTGC-CAAATGCTGGGTAAGATCATCGCC-CAACAAAATCAGTC CAGAGGCAAGGGACCGGG-GAAGAAAAATAGGAAGAAAAACCCGGAGAAGCCC-CAT TTCCCTCTAGCGACTGAAGATGACGTCAGGCAT-CACTTTACCCCTAGTGAGCGGCAAT TGTGTCTGTCGTCGATCCAGACTGCCTT-CAACCAGGGCGCTGGAACTTGTGCCGCGG CTGCCTCAGGGAGGATAAGTTACACTGTGGAGTT-TAGTTTGCCGACGCAACATACTGT GCGTCT-GATCCGCGCCACAGCATCACCCTCAG-CATGACTCGAG) of an N protein with positions 92 to 94 mutated to alanine were synthesized and cloned into a pCMV-HA vector, and a plasmid was extracted with an endotoxin-free plasmid extraction kit. 293T cells were transfected with pCMV-GS18N-HA, pCMV-GS18N92-94AA and pCMV-HA for 24 h separately; the cells were fixated with 4% paraformaldehyde for 10 min at room temperature, washed 5 times with pre-cooled PBS, and blocked with a blocking solution for 1 h at room temperature; a porcine C8 monoclonal antibody (1:500), a commercial N protein mouse-derived monoclonal antibody SR30A1 (1:50) and an HA rabbit-derived monoclonal antibody (1:500), and incubation was conducted overnight at 4° C. The cells were washed 5 times with pre-cooled PBS, 5 min for each time; a secondary antibody (1:50): FITC-labeled goat anti-pig antibody, an FITC-labeled goat anti-mouse antibody, and a Cy3-labeled goat anti-rabbit antibody that were fluorescently labeled were added; a reaction was conducted at 37° C. for 1 h in the dark, a product was washed with PBS 5 times and observed under a fluorescence microscope and photographed.

Figure 5:
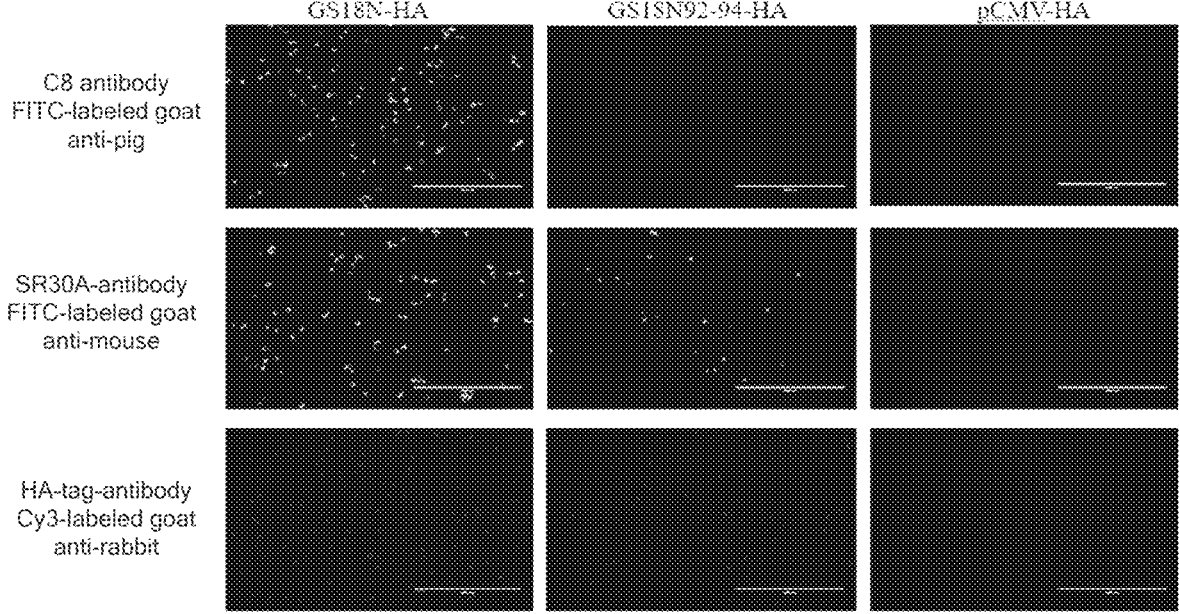
FIG. 5 shows reactivity detection results of the N protein of epitope deletion and a normal N protein with C8 monoclonal antibody after transfection into 293T cells.

The results were shown in FIG. 5. The results of indirect immunofluorescence assay show that the wild-type N protein can react with the two monoclonal antibodies. In contrast, the 92-94 mutant N protein cannot react with the C8 monoclonal antibody but can react with SR30A. This indicates that mutations at positions 92 to 94 can eliminate the epitope recognized by C8.

Example 5

Differentiation of Mouse Sera Immunized with GST-N Protein and GST-N92-94A Protein by N Protein Competitive ELISA Expression of recombinant protein: nucleic acid sequences of a wild-type N protein and N92-94A with positions 92 to 94 mutated to alanine were synthesized by a company, and ligated to a pGEX-6T-1 vector using BamHI and XhoI. The positive plasmids were transformed into BL-21 competent cells, single clones were selected for overnight culture, and expanded culture was conducted; 500 mL of a fresh bacterial solution was activated for 3 h, IPTG was added to a final concentration of 1 mmol/L, and induction was conducted 8 h at 37° C. Bacterial cells were collected by centrifugation of the bacterial solution at 8,000 rpm for 5 min, and a supernatant was discarded; cell pellets were mixed using 50 mL of an equilibration solution (including 0.15 M NaCl, 0.0027 M KCl, 0.01 M $Na_2HPO_4$, and 0.0018 M $KH_2PO_4$, adjusting a pH value to 7.3), and suspended on ice for sonication at 250 W for 15 min with 3 sec of intermittence and 3 sec of sonication; a product was centrifuged at 10,000 rpm for 10 min, a supernatant lysate and centrifuged pellets were collected, stored at 4° C., and detected by SDS-PAGE.

Recombinant protein purification: 4 mL of a GST-4FF resin was loaded into a column and allowed to settle naturally. The resin was rinsed and equilibrated with 5 times column volumes of an equilibration solution. The above protein sample was added to the resin column, mixed well, and combined overnight at 4° C., a flow rate was controlled to collect flow-through liquid. The column was washed 5 to 6 times with the equilibration solution, and a flow rate was controlled to collect some samples for testing. The column was washed 5 to 6 times with a reduced glutathione eluent (including 0.05 M Tris-HCl, 0.01 M GSH, at a pH value of 8.0) to elute a target protein and collect a sample. The collected sample was analyzed by SDS-PAGE and Western blotting.

Mice immunization: 1) antigen preparation: a concentration of recombinant protein was determined, a protein concentration was adjusted appropriately; the protein was mixed with a 201 adjuvant at 1:1 by volume, fully emulsified, and the mice were immunized at 100 μL in a dosage of 20 μg per mouse.

Animal immunization: 30 healthy female BALB/c mice aged 4-6 weeks were divided into three groups of 10 mice in each group (Table 2). An immunization method was subcutaneous immunization on the back of mice, and booster immunization was conducted on a third week. In a fifth week, secondary booster immunization was conducted. In a sixth week, blood was collected from eyeballs, and the mice were sacrificed. The serum was isolated and stored at −20° C. for later use. Detection was conducted by a laboratory-established PRRSV N protein antibody competitive ELISA method (patent 202110598030.7).

TABLE 2

| Grouping and immunization dosage of Balb/C mice | | |
|---|---|---|
| Groups | Immunogen | Immunization dosage |
| A | GST protein | 20 μg/mouse |
| B | N protein | 20 μg/mouse |
| C | N92-94 protein | 20 μg/mouse |

Figure 6:
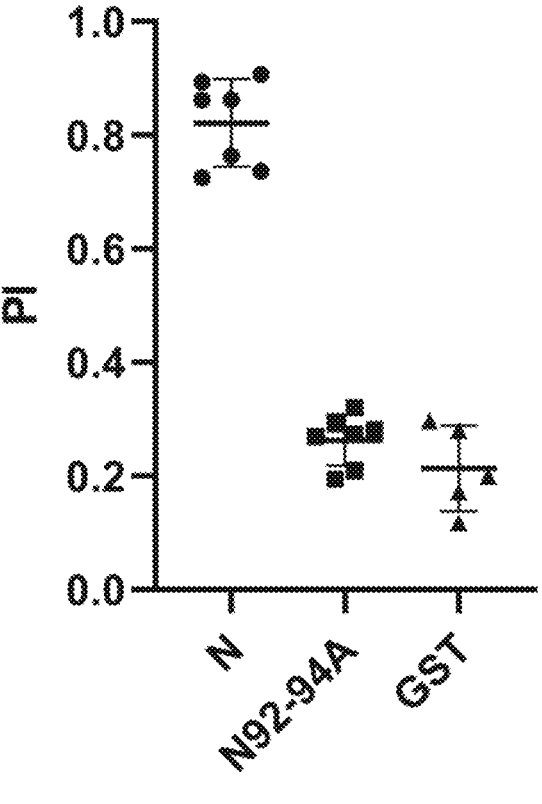
FIG. 6 shows the results of a mouse serum immunized with a prokaryotic expression N protein, an N92-94A mutant protein, and a GST protein detected using the N protein antibody competition ELISA method.

The results were shown in FIG. 6. The PRRSV N protein antibody competitive ELISA method can distinguish sera immunized with wild-type and epitope-deleted N proteins well, laying a foundation for the preparation of marked vaccines.

Figure 7:
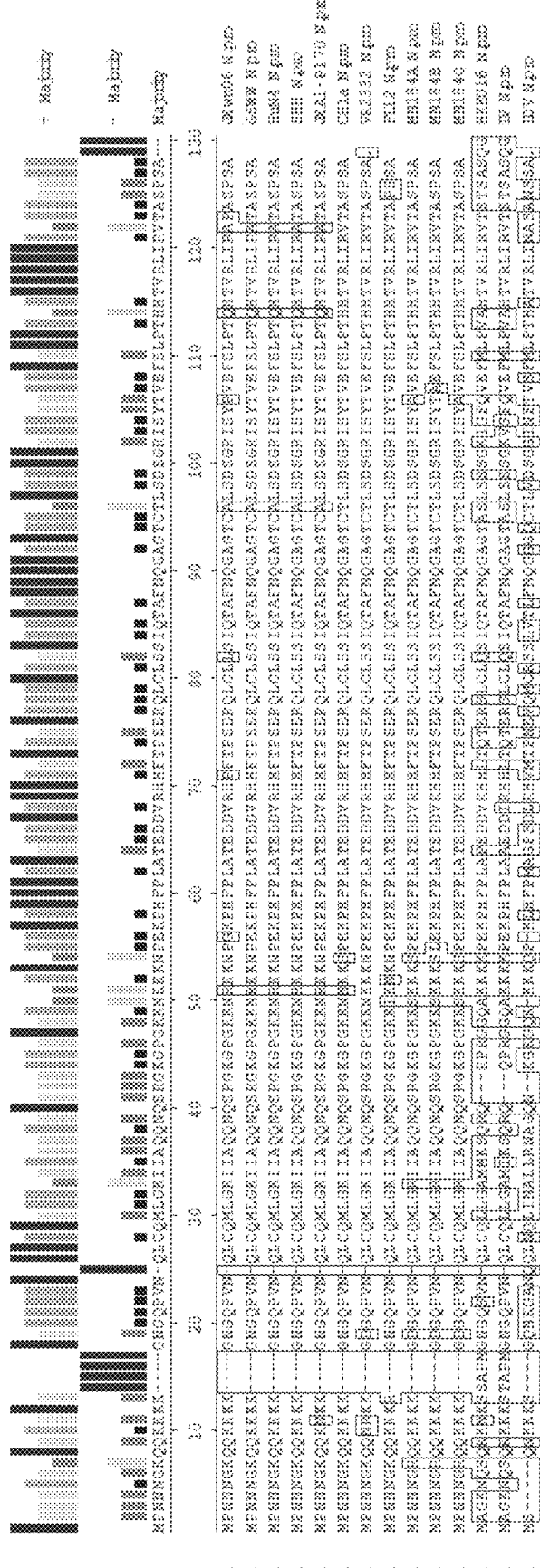
FIG. 7 shows a comparison result of an amino acid sequence of the N proteins from different genotypes of PRRSV strains and LDVs.

Alignment of N protein sequences of PRRSV type 1 and PRRSV type 2 (FIG. 7) and a lactate dehydrogenasee levating virus (LDV) strain reveals that the linear epitope is conserved in the type 2 strain. This indicates that the N protein linear epitope marker locus is suitable for construction of all candidate epitope deletion-marked vaccine strains for PRRSV type 2. A plasmid with deletion/mutation on single or multiple amino acids of the C-terminal epitope of the N protein is constructed using point mutation PCR and the existing PRRSV infectious clone full-length plasmid pGS-AB as a template, a full-length viral RNA is obtained by in vitro transcription, and virus rescue was conducted by transfecting Marc-145 cells. The successfully rescued recombinant strains are serially passaged on Marc-145 cells to prepare attenuated vaccines or inactivated vaccines; on the 14th day after birth, piglets are immunized with the candidate epitope-deleted vaccines, and blood is collected every 7 d after immunization to separate a serum, and a level of neutralizing antibodies is detected by a neutralization test; and the antibodies of N protein in serum are detected using an IDEXX PRRSV ELISA antibody detection kit and PRRSV N protein competitive ELISA antibody detection method.

Example 6

Rescue Method of Virus with Mutation at Positions 93 to 94 of N Protein

The mutation was conducted using a point mutation kit with a preserved half-length (positions 7606 to 15347) plasmid pGS-B containing a genome of a GSWW/2015 strain as a template, to obtain plasmids pGS-B/N93A and pGS-B/N93-94A. The pGS-B/N93A and the pGS-B/N93-94A were subjected to double enzyme digestion with Sph I and Nhe I, respectively, and ligated with a pGS-A (positions 1 to 7606) plasmid, to obtain full-length infectious clones, named pGS-B/N93A and pGS/N93-94A. The full-length plasmid was linearized with Acl I, purified by a phenol-chloroform method, and transcribed to synthesize a viral full-length RNA using an Ambion T7 in vitro transcription kit. BHK21 cells were transfected by electroporation, and cells and supernatants were collected 48 h later. After repeated freezing and thawing three times, Marc-145 cells were inoculated. Cells and supernatants were collected when more than 70% of the cells became diseased. RNA was extracted for PCR amplification, and sequenced to identify mutation loci. The mutant strains were successfully rescued and named rGSWW2015/N/S93A and rGSWW2015/N/S93A+D94A, respectively. The mutant virus was inoculated into Marc-145 cells, and indirect immunofluorescence detection was conducted 48 h later.

Figure 8:
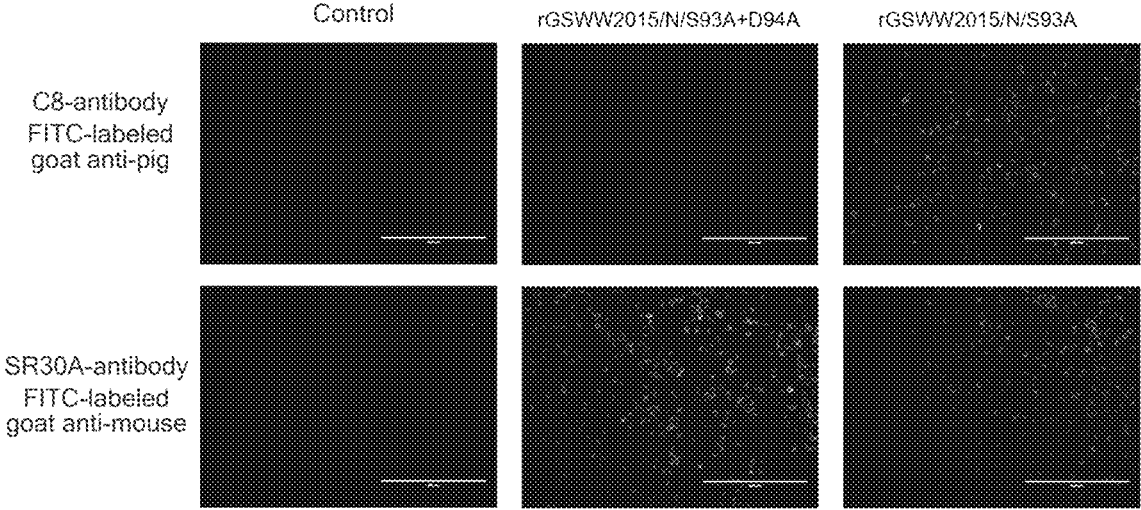
FIG. 8 shows indirect immunofluorescence results of an SR30A monoclonal antibody and the C8 monoclonal antibody 48 h after infection of Marc-145 cells with rGSWW2015/N/S93A and rGSWW2015/N/S93A+D94A.

The results in FIG. 8 show that the rGSWW2015/N/S93A strain can react with the C8 monoclonal antibody and a commercial monoclonal antibody SR30A, while the rGSWW2015/N/S93A+D94A strain can only react with the monoclonal antibody SR30A, not C8. These results indicate that the epitope-deleted strain is successfully constructed.

The above description of examples is merely provided to help illustrate the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. Various amendments to these embodiments are apparent to those of professional skill in the art, and the general principles defined herein may be implemented in other embodiments without departing from the spirit or scope of the present disclosure. Thus, the present disclosure is not limited to the examples shown herein but falls within the widest scope consistent with the principles and novel features disclosed herein.

---

What is claimed is:

1. A nucleocapsid protein (N protein) epitope mutation marker for preparing an epitope deletion-marked vaccine strain of type II porcine reproductive and respiratory syndrome virus (PRRSV), wherein N protein mutation marker is obtained by mutating the amino acids at positions 92 to 94 to alanine based on an amino acid sequence at positions 92 to 103 of a C-terminal of an N protein of the type II PRRSV; and the amino acid sequence at positions 92 to 103 of the C-terminal of the N protein of the type II PRRSV is set forth in SEQ ID NO: 1, wherein X1 is selected from the group consisting of T, P, and A; and X2 is selected from the group consisting of V and A.

2. A method for detecting the vaccine strain of type II PRRSV according to claim 1, the method comprises preparing a reagent or kit comprising a porcine single B cell antibody C8 of PRRSV N protein;

wherein the amino acid sequence of the porcine single B cell antibody C8 comprises the heavy chain variable region amino acid sequence HV1 of SEQ ID No: 63 and the light chain variable region amino acid sequence LV1 of SEQ ID No: 64.

* * * * *

SEQUENCE LISTING

```
<160> NUMBER OF SEQ ID NOS: 64

<210> SEQ ID NO 1
<211> LENGTH: 12
<212> TYPE: PRT
<213> ORGANISM: Artificial Sequence
<220> FEATURE:
<223> OTHER INFORMATION: N protein epitope mutation marker
<220> FEATURE:
<221> NAME/KEY: MISC_FEATURE
<222> LOCATION: (9)..(9)
<223> OTHER INFORMATION: X is T, P or A
<220> FEATURE:
<221> NAME/KEY: MISC_FEATURE
<222> LOCATION: (10)..(10)
<223> OTHER INFORMATION: X is V or A

<400> SEQUENCE: 1

Leu Ser Asp Gly Arg Ile Ser Tyr Xaa Xaa Glu Phe
1               5                   10

<210> SEQ ID NO 2
<211> LENGTH: 492
<212> TYPE: DNA
<213> ORGANISM: Artificial Sequence
<220> FEATURE:
<223> OTHER INFORMATION: CDS region of an N protein of a GSWW/2015
      strain

<400> SEQUENCE: 2
aagcttacca tgtacccata cgacgtccca gactacgctc caaataacaa cggcaagcag      60
```

-continued

```
caaaagaaaa agaaggggaa tggccagcca gtcaatcagc tgtgccaaat gctgggtaag    120
atcatcgccc aacaaaatca gtccagaggc aagggaccgg ggaagaaaaa taggaagaaa    180
aacccggaga agccccattt ccctctagcg actgaagatg acgtcaggca tcactttacc    240
cctagtgagc ggcaattgtg tctgtcgtcg atccagactg ccttcaacca gggcgctgga    300
acttgtgccc tgtcagattc agggaggata agttacactg tggagtttag tttgccgacg    360
caacatactg tgcgtctgat ccgcgccaca gcatcaccct cagcagacta caaggacgac    420
gacgacaagg gcgactacaa agatgacgat gataagatcg attacaaaga cgatgacgat    480
aagtgagaat tc                                                       492
```

```
<210> SEQ ID NO 3
<211> LENGTH: 15
<212> TYPE: PRT
<213> ORGANISM: Artificial Sequence
<220> FEATURE:
<223> OTHER INFORMATION: peptide fragment:GSWW15 N1

<400> SEQUENCE: 3

Met Pro Asn Asn Asn Gly Lys Gln Gln Lys Lys Lys Lys Gly Asn
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: peptide fragment:GSWW15 N2

<400> SEQUENCE: 4

Gly Lys Gln Gln Lys Lys Lys Lys Gly Asn Gly Gln Pro Val Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: peptide fragment:GSWW15 N3

<400> SEQUENCE: 5

Lys Lys Lys Gly Asn Gly Gln Pro Val Asn Gln Leu Cys Gln Met
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: peptide fragment:GSWW15 N4

<400> SEQUENCE: 6

Gly Gln Pro Val Asn Gln Leu Cys Gln Met Leu Gly Lys Ile Ile
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: peptide fragment:GSWW15 N5

<400> SEQUENCE: 7

Gln Leu Cys Gln Met Leu Gly Lys Ile Ile Ala Gln Gln Asn Gln
```

```
1               5               10              15

<210> SEQ ID NO 8
<211> LENGTH: 15
<212> TYPE: PRT
<213> ORGANISM: Artificial Sequence
<220> FEATURE:
<223> OTHER INFORMATION: peptide fragment:GSWW15 N6

<400> SEQUENCE: 8

Leu Gly Lys Ile Ile Ala Gln Gln Asn Gln Ser Arg Gly Lys Gly
1               5               10              15

<210> SEQ ID NO 9
<211> LENGTH: 15
<212> TYPE: PRT
<213> ORGANISM: Artificial Sequence
<220> FEATURE:
<223> OTHER INFORMATION: peptide fragment:GSWW15 N7

<400> SEQUENCE: 9

Ala Gln Gln Asn Gln Ser Arg Gly Lys Gly Pro Gly Lys Lys Asn
1               5               10              15

<210> SEQ ID NO 10
<211> LENGTH: 15
<212> TYPE: PRT
<213> ORGANISM: Artificial Sequence
<220> FEATURE:
<223> OTHER INFORMATION: peptide fragment:GSWW15 N8

<400> SEQUENCE: 10

Ser Arg Gly Lys Gly Pro Gly Lys Lys Asn Arg Lys Lys Asn Pro
1               5               10              15

<210> SEQ ID NO 11
<211> LENGTH: 15
<212> TYPE: PRT
<213> ORGANISM: Artificial Sequence
<220> FEATURE:
<223> OTHER INFORMATION: peptide fragment:GSWW15 N9

<400> SEQUENCE: 11

Pro Gly Lys Lys Asn Arg Lys Lys Asn Pro Glu Lys Pro His Phe
1               5               10              15

<210> SEQ ID NO 12
<211> LENGTH: 15
<212> TYPE: PRT
<213> ORGANISM: Artificial Sequence
<220> FEATURE:
<223> OTHER INFORMATION: peptide fragment:GSWW15 N10

<400> SEQUENCE: 12

Arg Lys Lys Asn Pro Glu Lys Pro His Phe Pro Leu Ala Thr Glu
1               5               10              15

<210> SEQ ID NO 13
<211> LENGTH: 15
<212> TYPE: PRT
<213> ORGANISM: Artificial Sequence
<220> FEATURE:
<223> OTHER INFORMATION: peptide fragment:GSWW15 N11

<400> SEQUENCE: 13

Glu Lys Pro His Phe Pro Leu Ala Thr Glu Asp Asp Val Arg His
1               5               10              15
```

```
<210> SEQ ID NO 14
<211> LENGTH: 15
<212> TYPE: PRT
<213> ORGANISM: Artificial Sequence
<220> FEATURE:
<223> OTHER INFORMATION: peptide fragment:GSWW15 N12

<400> SEQUENCE: 14

Pro Leu Ala Thr Glu Asp Asp Val Arg His His Phe Thr Pro Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: peptide fragment:GSWW15 N13

<400> SEQUENCE: 15

Asp Asp Val Arg His His Phe Thr Pro Ser Glu Arg Gln Leu Cys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: peptide fragment:GSWW15 N14

<400> SEQUENCE: 16

His Phe Thr Pro Ser Glu Arg Gln Leu Cys Leu Ser Ser Ile Gln
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: peptide fragment:GSWW15 N15

<400> SEQUENCE: 17

Glu Arg Gln Leu Cys Leu Ser Ser Ile Gln Thr Ala Phe Asn Gln
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: peptide fragment:GSWW15 N16

<400> SEQUENCE: 18

Leu Ser Ser Ile Gln Thr Ala Phe Asn Gln Gly Ala Gly Thr Cys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: peptide fragment:GSWW15 N17

<400> SEQUENCE: 19

Thr Ala Phe Asn Gln Gly Ala Gly Thr Cys Ala Leu Ser Asp Ser
1               5                   10                  15
```

-continued

```
<210> SEQ ID NO 20
<211> LENGTH: 15
<212> TYPE: PRT
<213> ORGANISM: Artificial Sequence
<220> FEATURE:
<223> OTHER INFORMATION: peptide fragment:GSWW15 N18

<400> SEQUENCE: 20

Gly Ala Gly Thr Cys Ala Leu Ser Asp Ser Gly Arg Ile Ser Tyr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: peptide fragment:GSWW15 N19

<400> SEQUENCE: 21

Ala Leu Ser Asp Ser Gly Arg Ile Ser Tyr Thr Val Glu Phe Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: peptide fragment:GSWW15 N20

<400> SEQUENCE: 22

Gly Arg Ile Ser Tyr Thr Val Glu Phe Ser Leu Pro Thr Gln His
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: peptide fragment:GSWW15 N21

<400> SEQUENCE: 23

Thr Val Glu Phe Ser Leu Pro Thr Gln His Thr Val Arg Leu Ile
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: peptide fragment:GSWW15 N22

<400> SEQUENCE: 24

Leu Pro Thr Gln His Thr Val Arg Leu Ile Arg Ala Thr Ala Ser Pro
1               5                   10                  15

Ser Ala

<210> SEQ ID NO 25
<211> LENGTH: 15
<212> TYPE: PRT
<213> ORGANISM: Artificial Sequence
<220> FEATURE:
<223> OTHER INFORMATION: peptide fragment:GSWW18 N1

<400> SEQUENCE: 25

Met Pro Asn Asn Asn Gly Arg Gln Gln Asn Lys Lys Lys Gly Asp
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: peptide fragment:GSWW18 N2

<400> SEQUENCE: 26

Gly Arg Gln Gln Asn Lys Lys Lys Gly Asp Gly Gln Pro Val Asn
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: peptide fragment:GSWW18 N3

<400> SEQUENCE: 27

Lys Lys Lys Gly Asp Gly Gln Pro Val Asn Gln Leu Cys Gln Met
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: peptide fragment:GSWW18 N4

<400> SEQUENCE: 28

Gly Gln Pro Val Asn Gln Leu Cys Gln Met Leu Gly Lys Ile Ile Ala
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: peptide fragment:GSWW18 N5

<400> SEQUENCE: 29

Gln Leu Cys Gln Met Leu Gly Lys Ile Ile Ala Gln Gln Arg Gln Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: peptide fragment:GSWW18 N6

<400> SEQUENCE: 30

Leu Gly Lys Ile Ile Ala Gln Gln Arg Gln Ser Lys Gly Arg Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: peptide fragment:GSWW18 N7

<400> SEQUENCE: 31

Ala Gln Gln Arg Gln Ser Lys Gly Arg Gly Pro Gly Lys Lys Asn
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: peptide fragment:GSWW18 N8

<400> SEQUENCE: 32

Ser Lys Gly Arg Gly Pro Gly Lys Lys Asn Lys Asn Lys Asn Leu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: peptide fragment:GSWW18 N9

<400> SEQUENCE: 33

Pro Gly Lys Lys Asn Lys Asn Lys Asn Leu Glu Lys Pro His Phe
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: peptide fragment:GSWW18 N10

<400> SEQUENCE: 34

Lys Asn Lys Asn Leu Glu Lys Pro His Phe Pro Leu Ala Thr Glu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: peptide fragment:GSWW18 N11

<400> SEQUENCE: 35

Glu Lys Pro His Phe Pro Leu Ala Thr Glu Asp Asp Val Arg His
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: peptide fragment:GSWW18 N12

<400> SEQUENCE: 36

Pro Leu Ala Thr Glu Asp Asp Val Arg His His Phe Thr Pro Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: peptide fragment:GSWW18 N13

<400> SEQUENCE: 37

Asp Asp Val Arg His His Phe Thr Pro Ser Glu Arg Gln Leu Cys
1               5                   10                  15

-continued

```
<210> SEQ ID NO 38
<211> LENGTH: 15
<212> TYPE: PRT
<213> ORGANISM: Artificial Sequence
<220> FEATURE:
<223> OTHER INFORMATION: peptide fragment:GSWW18 N14

<400> SEQUENCE: 38

His Phe Thr Pro Ser Glu Arg Gln Leu Cys Leu Ser Ser Ile Arg
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: peptide fragment:GSWW18 N15

<400> SEQUENCE: 39

Glu Arg Gln Leu Cys Leu Ser Ser Ile Arg Thr Ala Phe Asn Gln
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: peptide fragment:GSWW18 N16

<400> SEQUENCE: 40

Leu Ser Ser Ile Arg Thr Ala Phe Asn Gln Gly Ala Gly Thr Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: peptide fragment:GSWW18 N17

<400> SEQUENCE: 41

Thr Ala Phe Asn Gln Gly Ala Gly Thr Cys Thr Leu Ser Asp Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: peptide fragment:GSWW18 N18

<400> SEQUENCE: 42

Gly Ala Gly Thr Cys Thr Leu Ser Asp Ser Gly Arg Ile Ser Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: peptide fragment:GSWW18 N19

<400> SEQUENCE: 43

Thr Leu Ser Asp Ser Gly Arg Ile Ser Tyr Thr Val Glu Phe Ser
1               5                   10                  15

<210> SEQ ID NO 44
```

<211> LENGTH: 15
<212> TYPE: PRT
<213> ORGANISM: Artificial Sequence
<220> FEATURE:
<223> OTHER INFORMATION: peptide fragment:GSWW18 N20

<400> SEQUENCE: 44

Gly Arg Ile Ser Tyr Thr Val Glu Phe Ser Leu Pro Thr His His
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: peptide fragment:GSWW18 N21

<400> SEQUENCE: 45

Thr Val Glu Phe Ser Leu Pro Thr His His Thr Val Arg Leu Ile
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: peptide fragment:GSWW18 N22

<400> SEQUENCE: 46

Leu Pro Thr His His Thr Val Arg Leu Ile Arg Val Thr Thr Ser Pro
1               5                   10                  15

Ser Ala

<210> SEQ ID NO 47
<211> LENGTH: 384
<212> TYPE: DNA
<213> ORGANISM: Artificial Sequence
<220> FEATURE:
<223> OTHER INFORMATION: gene of an N protein with positions 92 to 94
      mutated to alanine

<400> SEQUENCE: 47
ggatccatgc caaataacaa cggcaagcag caaaagaaaa agaaggggaa tggccagcca        60
gtcaatcagc tgtgccaaat gctgggtaag atcatcgccc aacaaaatca gtccagaggc       120
aagggaccgg ggaagaaaaa taggaagaaa aacccggaga agccccattt ccctctagcg       180
actgaagatg acgtcaggca tcactttacc cctagtgagc ggcaattgtg tctgtcgtcg       240
atccagactg ccttcaacca gggcgctgga acttgtgccg cggctgcctc agggaggata       300
agttacactg tggagtttag tttgccgacg caacatactg tgcgtctgat ccgcgccaca       360
gcatcaccct cagcatgact cgag                                              384

<210> SEQ ID NO 48
<211> LENGTH: 123
<212> TYPE: PRT
<213> ORGANISM: Artificial Sequence
<220> FEATURE:
<223> OTHER INFORMATION: majority

<400> SEQUENCE: 48

Met Pro Asn Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
            20                  25                  30

```
Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
                100                 105                 110

Arg Leu Ile Arg Val Thr Ala Ser Pro Ser Ala
        115                 120
```

<210> SEQ ID NO 49
<211> LENGTH: 123
<212> TYPE: PRT
<213> ORGANISM: Artificial Sequence
<220> FEATURE:
<223> OTHER INFORMATION: JXwn06

<400> SEQUENCE: 49

```
Met Pro Asn Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Arg Lys Lys
        35                  40                  45

Asn Pro Gly Lys Pro His Phe Pro Leu Ala Thr Glu Asp Asp Val Arg
    50                  55                  60

His Pro Phe Thr Pro Ser Glu Arg Gln Leu Cys Leu Leu Ser Ile Gln
65                  70                  75                  80

Thr Ala Phe Asn Gln Gly Ala Gly Thr Cys Ala Leu Ser Asp Ser Gly
                85                  90                  95

Arg Ile Ser Tyr Pro Val Glu Phe Ser Leu Pro Thr Gln His Thr Val
                100                 105                 110

Arg Leu Ile Arg Ala Pro Ala Ser Pro Ser Ala
        115                 120
```

<210> SEQ ID NO 50
<211> LENGTH: 123
<212> TYPE: PRT
<213> ORGANISM: Artificial Sequence
<220> FEATURE:
<223> OTHER INFORMATION: GSWW

<400> SEQUENCE: 50

```
Met Pro Asn Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Arg Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Ala Leu Ser Asp Ser Gly
```

-continued

```
                85                  90                  95

Arg Ile Ser Tyr Thr Val Glu Phe Ser Leu Pro Thr Gln His Thr Val
                100                 105                 110

Arg Leu Ile Arg Ala Thr Ala Ser Pro Ser Ala
        115                 120

<210> SEQ ID NO 51
<211> LENGTH: 123
<212> TYPE: PRT
<213> ORGANISM: Artificial Sequence
<220> FEATURE:
<223> OTHER INFORMATION: HuN4

<400> SEQUENCE: 51

Met Pro Asn Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Arg Lys Lys
        35                  40                  45

Asn Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Ala Leu Ser Asp Ser Gly
                85                  90                  95

Arg Ile Ser Tyr Thr Val Glu Phe Ser Leu Pro Thr Gln His Thr Val
                100                 105                 110

Arg Leu Ile Arg Ala Thr Ala Ser Pro Ser Ala
        115                 120

<210> SEQ ID NO 52
<211> LENGTH: 123
<212> TYPE: PRT
<213> ORGANISM: Artificial Sequence
<220> FEATURE:
<223> OTHER INFORMATION: SHH

<400> SEQUENCE: 52

Met Pro Asn Asn Asn Gly Lys Gln Gln Lys Lys Lys Gly Asn Gly
1               5                   10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Arg Lys Lys
        35                  40                  45

Asn Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Ala Leu Ser Asp Ser Gly
                85                  90                  95

Arg Ile Ser Tyr Thr Val Glu Phe Ser Leu Pro Thr Gln His Thr Val
                100                 105                 110

Arg Leu Ile Arg Ala Thr Ala Ser Pro Ser Ala
        115                 120

<210> SEQ ID NO 53
<211> LENGTH: 123
```

<212> TYPE: PRT
<213> ORGANISM: Artificial Sequence
<220> FEATURE:
<223> OTHER INFORMATION: JXA1-P170

<400> SEQUENCE: 53

Met Pro Asn Asn Asn Gly Lys Gln Gln Lys Asn Lys Lys Gly Asn Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Arg Lys Lys
        35                  40                  45

Asn Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Ala Leu Ser Asp Ser Gly
                85                  90                  95

Arg Ile Ser Tyr Thr Val Glu Phe Ser Leu Pro Thr Gln His Thr Val
            100                 105                 110

Arg Leu Ile Arg Ala Thr Ala Ser Pro Ser Ala
        115                 120

<210> SEQ ID NO 54
<211> LENGTH: 123
<212> TYPE: PRT
<213> ORGANISM: Artificial Sequence
<220> FEATURE:
<223> OTHER INFORMATION: CH1a

<400> SEQUENCE: 54

Met Pro Asn Asn Asn Gly Lys Gln Arg Lys Lys Lys Lys Gly Asn Gly
1               5                   10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Ser Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 55
<211> LENGTH: 123
<212> TYPE: PRT
<213> ORGANISM: Artificial Sequence
<220> FEATURE:
<223> OTHER INFORMATION: VR2332

<400> SEQUENCE: 55

Met Pro Asn Asn Asn Gly Lys Gln Gln Asn Arg Lys Lys Gly Asp Gly
1               5                   10                  15

Gln Pro Val Asn Gln Leu Cys Gln Met Leu Gly Lys Ile Ile Ala Gln

```
                20              25              30

Gln Asn Gln Ser Arg Gly Lys Gly Pro Gly Lys Lys Asn Lys Lys
        35              40              45

Asn Pro Glu Lys Pro His Phe Pro Leu Ala Thr Glu Asp Asp Val Arg
    50              55              60

His His Phe Thr Pro Ser Glu Arg Gln Leu Cys Leu Ser Ser Ile Gln
65              70              75              80

Thr Ala Phe Asn Gln Gly Ala Gly Thr Cys Thr Leu Ser Asp Ser Gly
                85              90              95

Arg Ile Ser Tyr Thr Val Glu Phe Ser Leu Pro Thr His His Thr Val
                100             105             110

Arg Leu Ile Arg Val Thr Ala Ser Pro Ser Ala
        115             120

<210> SEQ ID NO 56
<211> LENGTH: 123
<212> TYPE: PRT
<213> ORGANISM: Artificial Sequence
<220> FEATURE:
<223> OTHER INFORMATION: FL-12

<400> SEQUENCE: 56

Met Pro Asn Asn Asn Gly Lys Gln Gln Lys Lys Lys Arg Gly Asn Gly
1               5               10              15

Gln Pro Val Asn Gln Leu Cys Gln Met Leu Gly Lys Ile Ile Ala Gln
                20              25              30

Gln Asn Gln Ser Arg Gly Lys Gly Pro Gly Lys Lys Ile Lys Asn Lys
        35              40              45

Asn Pro Glu Lys Pro His Phe Pro Leu Ala Thr Glu Asp Asp Val Arg
    50              55              60

His His Phe Thr Pro Ser Glu Arg Gln Leu Cys Leu Ser Ser Ile Gln
65              70              75              80

Thr Ala Phe Asn Gln Gly Ala Gly Thr Cys Thr Leu Ser Asp Ser Gly
                85              90              95

Arg Ile Ser Tyr Thr Val Glu Phe Ser Leu Pro Thr His His Thr Val
                100             105             110

Arg Leu Ile Arg Val Thr Ala Pro Ser Ser Ala
        115             120

<210> SEQ ID NO 57
<211> LENGTH: 123
<212> TYPE: PRT
<213> ORGANISM: Artificial Sequence
<220> FEATURE:
<223> OTHER INFORMATION: MN184A

<400> SEQUENCE: 57

Met Pro Asn Asn Asn Gly Arg Gln Gln Lys Lys Lys Gly Asp Gly
1               5               10              15

Gln Pro Val Asn Gln Leu Cys Gln Met Leu Gly Arg Ile Ile Ala Gln
                20              25              30

Gln Asn Gln Ser Arg Gly Lys Gly Pro Gly Lys Lys Ser Lys Lys Lys
        35              40              45

Ser Pro Glu Lys Pro His Phe Pro Leu Ala Thr Glu Asp Asp Val Arg
    50              55              60

His His Phe Thr Pro Ser Glu Arg Gln Leu Cys Leu Ser Ser Ile Gln
65              70              75              80
```

```
Thr Ala Phe Asn Gln Gly Ala Gly Thr Cys Thr Leu Ser Asp Ser Gly
                85                  90                  95

Arg Ile Ser Tyr Ala Val Glu Phe Ser Leu Pro Thr His His Thr Val
            100                 105                 110

Arg Leu Ile Arg Val Thr Ala Ser Pro Ser Ala
        115                 120
```

```
<210> SEQ ID NO 58
<211> LENGTH: 123
<212> TYPE: PRT
<213> ORGANISM: Artificial Sequence
<220> FEATURE:
<223> OTHER INFORMATION: MN184B

<400> SEQUENCE: 58

Met Pro Asn Asn Asn Gly Arg Gln Gln Lys Lys Lys Lys Gly Asp Gly
1               5                   10                  15

Gln Pro Val Asn Gln Leu Cys Gln Met Leu Gly Arg Ile Ile Ala Gln
            20                  25                  30

Gln Asn Gln Ser Arg Gly Lys Gly Pro Gly Lys Lys Ser Lys Lys Lys
        35                  40                  45

Ser Leu Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Ala Glu Phe Ser Leu Pro Thr His His Thr Val
            100                 105                 110

Arg Leu Ile Arg Val Thr Ala Ser Pro Ser Ala
        115                 120
```

```
<210> SEQ ID NO 59
<211> LENGTH: 123
<212> TYPE: PRT
<213> ORGANISM: Artificial Sequence
<220> FEATURE:
<223> OTHER INFORMATION: MN184C

<400> SEQUENCE: 59

Met Pro Asn Asn Asn Gly Arg Gln Gln Lys Lys Lys Lys Gly Asp Gly
1               5                   10                  15

Gln Pro Val Asn Gln Leu Cys Gln Met Leu Gly Arg Ile Ile Ala Gln
            20                  25                  30

Gln Asn Gln Ser Arg Gly Lys Gly Pro Gly Lys Lys Ser Lys Lys Lys
        35                  40                  45

Ser Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Ala Val Glu Phe Ser Leu Pro Thr His His Thr Val
            100                 105                 110

Arg Leu Ile Arg Val Thr Ala Ser Pro Ser Ala
        115                 120
```

```
<210> SEQ ID NO 60
```

```
<211> LENGTH: 128
<212> TYPE: PRT
<213> ORGANISM: Artificial Sequence
<220> FEATURE:
<223> OTHER INFORMATION: HKEU16

<400> SEQUENCE: 60

Met Ala Gly Lys Asn Gln Ser Gln Lys Lys Asn Lys Ser Ser Ala Pro
1               5                   10                  15

Met Gly Asn Gly Gln Ser Val Asn Gln Leu Cys Gln Leu Leu Gly Ala
            20                  25                  30

Met Met Lys Ser Gln Arg Gln Arg Pro Arg Gly Gly Gln Ala Lys Lys
        35                  40                  45

Lys Lys Pro Glu Lys Pro His Phe Pro Leu Ala Pro Glu Asp Asp Val
    50                  55                  60

Arg His His Leu Thr Gln Thr Glu Arg Ser Leu Cys Leu Gln Ser Ile
65                  70                  75                  80

Gln Thr Ala Phe Asn Gln Gly Ala Gly Thr Ala Ser Leu Ser Ser Ser
                85                  90                  95

Gly Lys Ile Gly Phe Gln Val Glu Phe Met Leu Pro Val Ala His Thr
            100                 105                 110

Val Arg Leu Ile Arg Val Thr Ser Thr Ser Ala Ser Gln Gly Ala Ile
            115                 120                 125

<210> SEQ ID NO 61
<211> LENGTH: 128
<212> TYPE: PRT
<213> ORGANISM: Artificial Sequence
<220> FEATURE:
<223> OTHER INFORMATION: LV

<400> SEQUENCE: 61

Met Ala Gly Lys Asn Gln Ser Gln Lys Lys Lys Lys Ser Thr Ala Pro
1               5                   10                  15

Met Gly Asn Gly Gln Pro Val Asn Gln Leu Cys Gln Leu Leu Gly Ala
            20                  25                  30

Met Ile Lys Ser Gln Arg Gln Gln Pro Arg Gly Gly Gln Ala Lys Lys
        35                  40                  45

Lys Lys Pro Glu Lys Pro His Phe Pro Leu Ala Ala Glu Asp Asp Ile
    50                  55                  60

Arg His His Leu Thr Gln Thr Glu Arg Ser Leu Cys Leu Gln Ser Ile
65                  70                  75                  80

Gln Thr Ala Phe Asn Gln Gly Ala Gly Thr Ala Ser Leu Ser Ser Ser
                85                  90                  95

Gly Lys Val Ser Phe Gln Val Glu Phe Met Leu Pro Val Ala His Thr
            100                 105                 110

Val Arg Leu Ile Arg Val Thr Ser Thr Ser Ala Ser Gln Gly Ala Ser
            115                 120                 125

<210> SEQ ID NO 62
<211> LENGTH: 115
<212> TYPE: PRT
<213> ORGANISM: Artificial Sequence
<220> FEATURE:
<223> OTHER INFORMATION: LDV

<400> SEQUENCE: 62

Met Ser Gln Asn Lys Lys Lys Ser Gly Gln Asn Lys Gly Ala Asn Gln
1               5                   10                  15
```

-continued

Gln Leu Asn Gln Leu Ile Asn Ala Leu Leu Arg Asn Ala Gly Gln Asn
        20              25              30

Lys Gly Lys Gly Gln Lys Lys Lys Gln Pro Lys Leu His Phe Pro
        35              40              45

Met Ala Gly Phe Ser Asp Leu Arg His Val Met Thr Pro Asn Glu Val
    50              55              60

Gln Met Cys Arg Ser Ser Leu Val Thr Leu Phe Asn Gln Gly Gly Gly
65              70              75              80

Gln Cys Thr Leu Val Asp Ser Gly Gly Ile Asn Phe Thr Val Ser Phe
            85              90              95

Met Leu Pro Thr His Ala Thr Val Arg Leu Ile Asn Ala Ser Ala Asn
        100             105             110

Ser Ser Ala
        115

<210> SEQ ID NO 63
<211> LENGTH: 108
<212> TYPE: PRT
<213> ORGANISM: Artificial Sequence
<220> FEATURE:
<223> OTHER INFORMATION: heavy chain variable region amino acid sequence
      HV1

<400> SEQUENCE: 63

Gly Leu Val Gln Pro Gly Gly Ser Leu Arg Leu Ser Cys Val Ala Ser
1               5               10              15

Gly Phe Thr Phe Ser Ser Tyr Ile Val Thr Trp Val Arg Gln Ser Pro
            20              25              30

Gly Lys Gly Leu Glu Trp Leu Ala Gly Thr Gly Val Gly Glu Tyr Ala
        35              40              45

Leu Tyr Tyr Arg Asn Ser Val Arg Gly Arg Phe Thr Leu Ser Arg Asp
    50              55              60

Asn Ser Gln Asn Thr Ala Tyr Leu Gln Met Asn Ser Leu Arg Val Glu
65              70              75              80

Glu Thr Gly Arg Tyr Phe Cys Arg Arg Gly Ala Ala Glu Ser Val Asp
            85              90              95

Leu Trp Gly Pro Gly Val Glu Val Val Val Ser Ser
        100             105

<210> SEQ ID NO 64
<211> LENGTH: 106
<212> TYPE: PRT
<213> ORGANISM: Artificial Sequence
<220> FEATURE:
<223> OTHER INFORMATION: light chain variable region amino acid sequence
      LV1

<400> SEQUENCE: 64

Gln Glu Pro Ala Met Ser Val Ser Leu Gly Gly Thr Val Thr Leu Thr
1               5               10              15

Cys Ala Phe Ser Ser Gly Ser Val Thr Arg Ser His Trp Pro Ser Trp
            20              25              30

Phe Gln Leu Thr Pro Gly Gln Pro Pro Arg Thr Leu Ile Val Ser Thr
        35              40              45

Asp Ser Arg Pro Thr Gly Val Pro Ser Arg Phe Ser Gly Ala Ile Ser
    50              55              60

Gly Tyr Lys Ala Ala Leu Thr Ile Thr Gly Ala Gln Pro Glu Asp Glu
65              70              75              80

-continued

```
Ala Asp Tyr Val Cys Gly Val Tyr Phe Thr Phe Thr Lys Arg Pro Phe
                85                  90                  95

Gly Gly Gly Thr His Leu Thr Val Leu Gly
            100                 105
```